US012691286B2

(12) United States Patent
Burnam

(10) Patent No.: US 12,691,286 B2
(45) Date of Patent: Jul. 28, 2026

(54) METHOD USING TREND ANALYSIS FOR CARDIAC TREATMENT WITH CALIBRATED AND POSITIONALLY CORRECTED BLOOD PRESSURE WATCHES, PRESSURE-PACE ALGORITHMS, ARTIFICIAL INTELLIGENCE AND THORACIC ELECTRICAL BIOIMPEDANCE

(71) Applicant: BaroPace, Inc., Ashland, OR (US)

(72) Inventor: Michael Burnam, Ashland, OR (US)

(73) Assignee: BaroPace, Inc., Ashland, OR (US)

( * ) Notice: Subject to any disclaimer, the term of this patent is extended or adjusted under 35 U.S.C. 154(b) by 687 days.

(21) Appl. No.: 18/042,708

(22) PCT Filed: Jul. 21, 2021

(86) PCT No.: PCT/US2021/042622
§ 371 (c)(1),
(2) Date: Feb. 23, 2023

(87) PCT Pub. No.: WO2022/046326
PCT Pub. Date: Mar. 3, 2022

(65) Prior Publication Data
US 2023/0355991 A1    Nov. 9, 2023
Related U.S. Application Data

(60) Provisional application No. 63/069,633, filed on Aug. 24, 2020.

(51) Int. Cl.
| | |
|---|---|
| *A61N 1/362* | (2006.01) |
| *A61B 5/00* | (2006.01) |
| *A61B 5/021* | (2006.01) |
| *A61B 5/024* | (2006.01) |
| *A61B 5/053* | (2021.01) |
| *A61N 1/365* | (2006.01) |

(52) U.S. Cl.
CPC ................................. *A61N 1/36564* (2013.01)

(58) Field of Classification Search
CPC .............. A61N 1/36564; A61N 1/3627; A61N 1/36521; A61N 1/36571; A61N 1/36585;
(Continued)

(56) References Cited

U.S. PATENT DOCUMENTS

| | | |
|---|---|---|
| 2015/0327776 A1 | 11/2015 | Zhang et al. |
| 2017/0238812 A1 | 8/2017 | Atlas |

(Continued)

FOREIGN PATENT DOCUMENTS

| | | |
|---|---|---|
| CA | 3116605 A1 | 5/2020 |
| WO | 2018222651 A1 | 12/2018 |

(Continued)

OTHER PUBLICATIONS

International Search Report and Written Opinion issued in International Application No. PCT/US2021/042622 on Jan. 26, 2022 (15 pages).

(Continued)

*Primary Examiner* — Carl H Layno
*Assistant Examiner* — Anh-Khoa N Dinh
(74) *Attorney, Agent, or Firm* — DLA Piper LLP (US)

(57) ABSTRACT

A method of using thoracic electrical bioimpedance (TEB) as a component in a real-time closed-loop system to treat drug resistant hypertension (DRH) or diastolic heart failure (called HFpEF in patients with pacemakers using machine learning/AI and an algorithm (PressurePace—see the incorporated specifications) utilizing a "micro-interval" or continually updated trending method with the pacemaker's hardware/software as the source of the bioimpedance measurement, e.g. OptiVol. An apparatus for performing the method, and software instructions stored on a tangible medium for controlling a computer or processor to perform the method are included.

14 Claims, 8 Drawing Sheets

(58) Field of Classification Search

CPC .............. A61N 1/3702; A61N 1/3628; A61N 1/37282; A61N 1/057; A61N 1/36114; A61N 1/36139; A61N 1/365; A61N 1/37205; A61N 1/37518; A61N 1/3756; A61N 1/378; A61N 1/39622; A61B 5/7264; A61B 5/4836; A61B 5/024; A61B 5/053; A61B 5/021; A61B 5/0205; G16H 20/40; G16H 40/40; G16H 50/20; G16H 40/67

See application file for complete search history.

(56) References Cited

U.S. PATENT DOCUMENTS

2019/0060602 A1    2/2019  Tran et al.
2019/0232065 A1*   8/2019  Perschbacher ......... A61B 5/021

FOREIGN PATENT DOCUMENTS

WO       2020096982 A1     5/2020
WO       2020210060 A1    10/2020
WO       WO-2021194543 A1 *  9/2021   ........... A61N 1/3628

OTHER PUBLICATIONS

Min et al. Thoracic bioimpedance as a basis for pacing control. Apr. 20, 1999 (Apr. 20, 1999). [retrieved on Dec. 18, 2021]. Retrieved from the Internet: <URL: https://pubmed.ncbi.nlm.nih.gov/10372164/> pp. 155-166.

Walsh III et al. Novel Wireless Devices for Cardiac Monitoring. Aug. 12, 2015 (Aug. 12, 2015). [retrieved on Dec. 18, 2021]. Retrieved from the Internet: <URL: https://www.ncbi.nlm.nih.gov/pmc/articles/PMC4135373/pdf/nihms610563.pdf> pp. 1-19.

Office Action for Canadian Patent Application No. 3,192,619, mailed Nov. 25, 2025, 7 pages.

* cited by examiner

PP And Rate Modulation

1

METHOD USING TREND ANALYSIS FOR CARDIAC TREATMENT WITH CALIBRATED AND POSITIONALLY CORRECTED BLOOD PRESSURE WATCHES, PRESSURE-PACE ALGORITHMS, ARTIFICIAL INTELLIGENCE AND THORACIC ELECTRICAL BIOIMPEDANCE

CROSS-REFERENCE TO RELATED APPLICATIONS

This patent application is a continuation of and claims the benefit of priority to International Application No. PCT/US2021/042622, filed on Jul. 21, 2021, now published as WO 2022/046326 A1, which claims priority to U.S. Provisional Application No. 63/069,633, filed on Aug. 24, 2020, the entireties of each of which is incorporated herein by reference.

INCORPORATED SPECIFICATIONS

Incorporated herein by reference, as if set out in the entirety, are US provisional patent application entitled, Method of Treatment of Drug Resistant Hypertension by Electrically Stimulating the Right Atrium to Create Inhibition of the Autonomic Nervous System, filed on May 5, 2020, Ser. No. 63/101,544; U.S. provisional patent application 62/833,052, filed on Apr. 12, 2019; U.S. provisional patent applications 62/757,559, filed on Nov. 8, 2018; PCT Patent Application, PCT/US2020/25477, filed on Mar. 27, 2020; and PCT/US2019/59703, filed on Nov. 4, 2019. Hereinafter collectively called the incorporated specifications.

BACKGROUND

Field of the Technology

The invention relates to the field of cardiac medical systems and medical methodologies, and, more particularly, to medical devices that monitor cardiac health, such as in CPC classes A61B 5/0537 (20130101); A61N 1/36521 (20130101); A61N 1/3702 (20130101); A61B 5/0538 (20130101); A61B 5/7275 (20130101); A61N 1/37258 (20130101).

Description of the Prior Art

Chronic heart failure (HF) occurs when a heart is unable to consistently pump blood at an adequate rate in response to the filling pressure. To improve the ability of the heart to pump blood, congestive heart failure patients, classified as having New York Heart Association (NYHA) class status of II to IV HF, may require implantable medical devices (IMDs) such as implantable cardioverter defibrillators (ICDs) and cardiac resynchronization therapy devices with defibrillation capability (CRT-Ds). Despite using IMDs to improve heart function, some HF patients may require hospitalization. Global health care systems incur billions of dollars each year due to heart failure hospitalizations (HFHs). Identifying patients at risk of a heart failure event (HFE) (e.g. HFH) to enable timely intervention and prevent expensive hospitalization remains a challenge. ICDs and CRT-Ds are configured to acquire data for a variety of diagnostic metrics that change with HF status and collectively have the potential to signal an increasing risk of HFE. Diagnostic parameter data collected by IMDs include activity, day and night heart rate, atrial tachycardia/atrial fibrillation (AT/AF) burden, mean rate during AT/AF, percent CRT pacing, number of shocks, and intrathoracic impedance. Additionally, preset or programmable thresholds for diagnostic metrics, when crossed, can trigger a notification, referred to as device observation. Each device observation is recorded in an IMD report and can be transmitted to an external healthcare system. Numerous healthcare systems (i.e. CARELINK® from Medtronic) are able to automatically notify health care workers of potential issues associated with a patient.

While recently we have focused on the autonomic nervous system (ANS) as a major determinant of systemic vascular resistance (SVR), but the focus heretofore has not been on the causative mechanism with the goal being to reduce systemic vascular resistance (SVR) by right atrial (RA) pacing and a lowered blood pressure. Other factors affecting systemic vascular resistance (SVR) include chemicals released in the body, such as epinephrine and norepinephrine.

Blood Pressure is the expression of the resistance in arteries to blood flow according to "Ohm's Law" applied to fluid dynamics. V=IR, where V is blood pressure, I is cardiac output, and R is the resistance to blood flow also known as systemic vascular resistance (systemic vascular resistance (SVR)).

Systemic vascular resistance (SVR) can be calculated if cardiac output (CO), mean arterial pressure (*), and central venous pressure (CVP) are known. In other words, SVR= (MAP−CVP)/CO. The units for systemic vascular resistance (SVR) are most commonly expressed as pressure (mmHg) divided by cardiac output (mL/min). There are two variables in the equation. We cannot easily measure RA pressure without an invasive method or expensive and time-consuming ultrasound method. But in most instances, the magnitude of RA pressure does not change significantly except in certain extreme disease states most commonly associated with lung disease. If we exclude such patients from the measurement cohort, we can assume RA pressure is fairly constant at around 10 mmHg and keep it as a constant.

Cardiac output is much more difficult to measure non-invasively. Some equipment does exist to do it, for example photoelectric plethysmography, but this is impractical for clinical purposes. Another method is thoracic electrical bioimpedance. Thoracic electrical bioimpedance (TEB) is a non-invasive method of cardiac output monitoring. It is based on the hypothesis which considers the thorax as a cylinder perfused with fluid with specific resistivity. It measures the electrical resistance of the thorax to a high frequency, low amplitude current. Impedance cardiography (ICG) is a noninvasive technology measuring total electrical conductivity of the thorax and its changes in time to process continuously a number of cardiodynamic parameters, such as stroke volume, SV, heart rate, HR, cardiac output, CO, ventricular ejection time, VET, pre-ejection period and used to detect the impedance changes caused by a high-frequency, low magnitude current flowing through the thorax between additional two pairs of electrodes located outside of the measured segment. The sensing electrodes also detect the ECG signal, which is used as a timing clock of the system.

Some Medtronic defibrillator pacemakers (CRT devices) have a component or operating protocol carrying the brand, OptiVol (Medtronics, Minneapolis, MN). OptiVol tracks intrathoracic electrical bioimpedance changes over time, not to estimate cardiac output, but to estimate thoracic fluid content which was hoped to be a way of diagnosing and treating heart failure, a pathologic situation where the lungs, hence the thorax, fill with fluid. Clinical data suggest that changes in intrathoracic impedance and fluid accumulation in the thoracic cavity or lungs are inversely correlated. As the patient's lungs become congested, intrathoracic impedance tends to decrease. Similarly, an increase in intrathoracic impedance may indicate the patient's lungs are becoming drier. OptiVol monitoring to predict worsening heart failure does not replace assessments which are part of standard clinical practice.

Because water (blood) is an electrical volume conductor, bioimpedance operates on the premise that the oscillation of a water-filled space oscillating within a passive electrical field can be detected as a change in electrical impedance. To accomplish this, electrodes are placed in a three-dimensional array around the oscillating column of water (blood) and hooked up to amplifiers and electronic signal processors to detect the impedance change. The magnitude of the oscillation is proportional to the oscillating volume. However, in order for a valid measurement to be made first the electrodes have to be stable and placed three dimensionally far apart and surrounding the oscillating fluid column. Second, the underlying signal processing algorithms assume that the oscillations of the fluid column are fairly uniform and not complex in shape. Third, there are other fluid filled spaces in the thorax besides the heart, most importantly the lungs which can fill with fluid in heart failure, and oscillate with each breath.

Therefore, Medtronic's OptiVol in a pacemaker has not been highly successful as a cardiac methodology because: 1) The heart is not a regular shape; and 2) The electrodes are inside the pacemaker can, resulting in a very small volume of detection, and placed in a position which does not surround the heart which is the targeted oscillator. In an effort to avoid these limitations the current conventional use of TEB places electrodes at the four extremes of the thorax, front and back including a necklace worn around the neck. The dimension of the pacemaker can are much too small and inappropriately placed, which renders OptiVol as an unsuitable option for cardiac monitoring. Fluid in the lungs turns out to be a bigger signal than the heart and the greater the degree of heart failure, the more the OptiVol signal which can "drown" out the desired heart signal.

Almost all medical researchers thus gave up on TEB for measuring cardiac output for the above limitations of the OptiVol methodology. These same limitations exclude the possibility of using TEB to measure systemic vascular resistance (SVR) as a discrete and accurate measurement, because it requires that you know cardiac output as the key component of the equation along with mean arterial pressure. The use of TEB for detection of fluid in the lungs was not a good pre-clinical indicator of developing lung water or heart failure, because the lead array hardly spans the volume occupied by the lungs.

What is needed is a method wherein PressurePace algorithms using AI may be combined with calibrated and positionally corrected blood pressure watches with pacemakers with TEB or OptiVol features What is needed is a more direct measurement of SVR for blood pressure reduction.

What is needed is a more physiologic pacemaker.

BRIEF SUMMARY

Thoracic electrical bioimpedance TEB has been used to assess and treat hypertension and heart failure, including an estimation of systemic vascular resistance (SVR), but it has never been used as a component in a real-time closed-loop system to treat drug resistant hypertension (DRH) or diastolic heart failure (called HFpEF in patients with pacemakers using machine learning/AI and an algorithm (PressurePace—see the incorporated specifications) utilizing a "micro-interval" or continually updated trending method with the pacemaker's hardware/software as the source of the bioimpedance measurement, e.g. OptiVol.

This combination is advantageous for the treatment of DRH and HFpEF in patients with pacemakers and better than systems using skin electrodes for autonomic nervous system (ANS) function, because the measurement includes all factors resulting in systemic vascular resistance (SVR) which are more than ANS function alone. Thus, the combination is one step closer to the true physiologic endpoint. The use of TEB for diagnosis and treatment includes decision-making based on trending and not on absolute value determinations that can be variable. A real-time closed loop treatment algorithm for DRH and DRH with HFpEF utilizing machine learning/AI including bioimpedance in a closed loop to estimate cardiac output and calculate systemic vascular resistance (SVR) is a valuable adjunct to measuring blood pressure alone.

The same closed loop autonomous running system, where a component is a bioimpedance measurement device (hardware and software), could in a further embodiment be integrated into a pacemaker including its leads implanted in the human body. Another embodiment includes the same closed loop system where the bioimpedance module is all, or partly outside the body and the electrode array is worn externally by the patient. The most common of such an embodiment would be in the form of a necklace.

The precision of the TEB measurement is not accurate, but this lack of precision is not relevant where only relative trends of increasing or decreasing measurement are needed. Using an incremental measurement approach that allows us to use inaccurate blood pressure watches, the simultaneous use of OptiVol or TEB to estimate cardiac output trends is an indirect measure of systemic vascular resistance (SVR), which can be used with a therapeutic algorithm called PressurePace and artificial intelligence (AI). A machine-learning subroutine may be stored and used on the patient's smartphone or smartwatch, rather than a fully functional AI solution, which is accessed through an encrypted internet link to a secure mainframe. Microtrending could be done locally with the patient using the computer power on a smartphone using machine learning methods.

Patients with pacemakers having OptiVol can be monitored by PressurePace and AI, if patients with severe lung disease are excluded to keep RA pressure constant. OptiVol or TEB thus becomes useful for a new goal, namely as an indirect measure of systemic vascular resistance (SVR).

Nevertheless, there is a signal from OptiVol or TEB that tracks cardiac output when the patient is not in heart failure and does change in a predicted direction when heart failure develops. We use trending, not absolute values of measured output. systemic vascular resistance (SVR) are better than skin electrode trends as systemic vascular resistance (SVR) encompasses all the causative factors, not just ANS input to vascular resistance. Precise or accurate measurements of systemic vascular resistance (SVR) are not required, but only trends of systemic vascular resistance (SVR), which OptiVol can supply for patients not in heart failure. The use of a trending AI-based algorithm where the direction of change in systemic vascular resistance (SVR) for each increment of time is what is needed, more than an absolute value.

If we use a trending AI-based algorithm to calculate a trend in systemic vascular resistance (SVR), and the algorithm detects an increased bioimpedance over a matter of hours or days, the algorithm can signal the possible development of increased lung water. The patterns of changes in systemic vascular resistance (SVR) due to pacing and blood pressure dynamics are very different than the slow onset of heart failure, absent a cardiac catastrophic event like a massive heart attack. PressurePace algorithm is "taught" the difference using AI between patterns of changes in systemic vascular resistance (SVR) due to pacing and blood pressure dynamics and the slow onset of heart failure. The algorithm is always be on the lookout for this difference from moment to moment. Thus, OptiVol or TEB is used with PressurePace and AI to trend systemic vascular resistance (SVR) to detect the occurrence of increased lung water or most likely heart failure.

The ability to reliably measure systemic vascular resistance (SVR) trends breaks down somewhat if RA pressure increases. An initial high, stable RA pressure has no adverse effect, rather only when the RA pressure changes. Even so, the magnitude of RA pressure is so small that it would likely make little difference. Increased lung water would also perturb the measurement by changing the trending to look like artificially increased systemic vascular resistance (SVR). But AI could detect such a trend by noting the rate of rise of the change which would be outside of what would be expected for systemic vascular resistance (SVR) in the same patient. The AI would have an archive of typical systemic vascular resistance (SVR) changes (moment to moment) of the monitored patient, and could easily detect an overlay trend that "moves" with a different pattern. The PressurePace algorithm with AI would already have been "taught" the kinds of patterns to expect with increased lung water.

To verify the disclosed methodology we would do a pilot study in parallel with what we call our chairside protocol with a first group of patients. Conventional bioimpedance TEB units are available to measure systemic vascular resistance (SVR) or at least trends that are accepted as valid. A comparison with a second group of patients with Medtronic pacers and hypertension, whose pacemakers have OptiVol, are also monitored and run side by side with the first group as we increase RA pacing to change blood pressure. RA pacing would at least temporarily increase cardiac output for a few minutes until homeostasis sets in, and that would cause a drop in systemic vascular resistance (SVR). If OptiVol trends in the right direction along with the conventional TEB unit, a PressurePace algorithm with AI is then included to the pacing protocol: The combination of a blood pressure device, PressurePace with AI and OptiVol detects systemic vascular resistance (SVR) changes as an adjunct to the real time closed-loop AI powered pacing system.

It is within the scope of the invention to use OptiVol to detect early increases in lung water by processing the OptiVol data in a different manner than previously used to predict heart failure.

Furthermore, since TEB and systemic vascular resistance (SVR) can be integrated into a measure of cardiac output (even if not in the actual liters/min metric), a physiologic pacemaker as disclosed can be integrated into Implantable electronic cardiovascular devices (IECD's) for diagnostic or therapeutic treatment of heart failure, including but not limited to implantable cardioverter defibrillators (ICDs), cardiac resynchronization therapy devices with defibrillation capability (CRT-Ds) and cardiac resynchronization therapy pacemaker (CRT-P's). The use of trending measurements of systemic vascular resistance (SVR) allows the real time use of conventional blood pressure wrist watches, which are inaccurate and inexpensive, for much smoother changes in pacing rate and hence in a physiologic response.

The illustrated embodiments of the invention also include a trend analysis method that: 1) Improves the accuracy of physiologic sensor measurements for use in dynamic treatment algorithms when repetitive calibration of the sensors is not possible or practical, and/or the discrete measurement has inherent variabilities; 2) Includes a hierarchal subroutine based upon machine learning that integrates additional variables to better achieve the treatment goal (the system is scalable); 3) Unlike medication, makes dynamic treatment decisions, including the absence of therapy for part of the day and is available 24 hours a day; 4) Improves the safety and efficacy of rate modulation; 5) Enhances the clinical utility of Medtronic's OptiVol protocol; and 6) Provides a tool for evaluation of any intervention that affects blood pressure.

In one embodiment a use of PressurePace (PP) as set forth in the incorporated specification is used to treat hypertension in patients with pacemakers and no other physiologic sensors supplying inputs, except for rate modulation sensors (e.g. motion sensor and respiratory rate sensor) resident in the pacemaker. The available sensor inputs for pacemaker rate modulation include: heart rate (HR); respiratory rate; a motion sensor; and right atrial (RA) pacing rate. Inputs from a blood pressure smart watch include: blood pressure (blood pressure); and arm position (i.e. the arm wearing the watch) indicating above thorax level, at thorax level or below thorax level.

In one embodiment, the blood pressure measuring device is a blood pressure smart watch. The blood pressure watch has a position sensor, which previously in conventional smart watches with a position sensor were used only to sense when the arm swings. The PressurePace algorithm is resident in the smart watch. The blood pressure smart watch includes a feature that allows the patient to "signal" an adverse event, such as an initiated change in heart rate that has possibly resulted in an adverse symptom. This event could serve to suspend treatment, resume baseline settings prior to therapy initiation, and continue monitoring. The blood pressure smart watch in the illustrated embodiment includes an audible and flashing indicator that alerts the patient as directed by PP as described below.

In addition, the smart watch or smartphone may be linked via blue tooth to a blood pressure sensor embodied in a finger ring.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Optional Calibration of Blood Pressure Smart Watch

Figure 1:
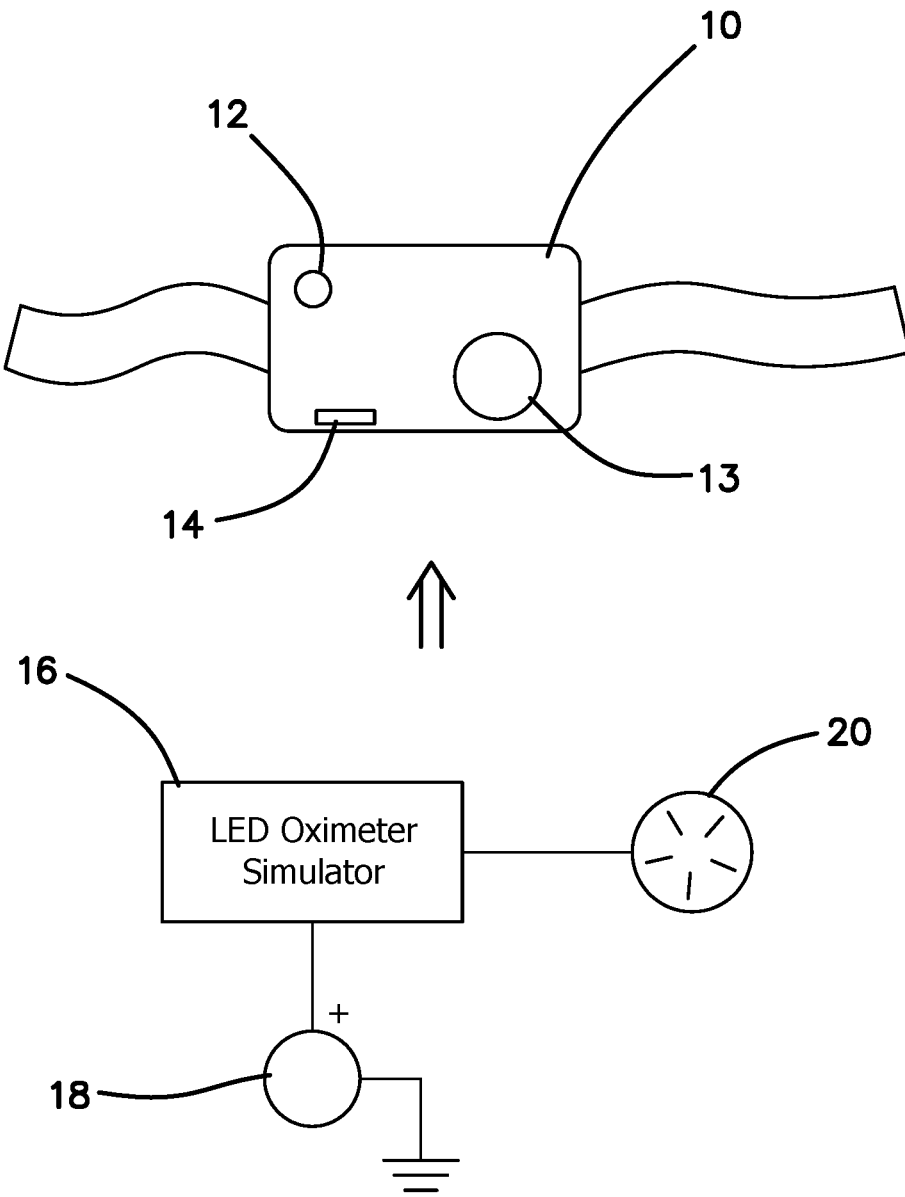
FIG. 1 is a diagram of a blood pressure watch worn on the wrist with a diagrammatic depiction of sensors and circuitry in it that allows it to be calibrated electronically and secondarily corrected for arm position.

Turn now and consider how baseline value determinations are made in the illustrated embodiment using an optional calibration of the blood pressure watch. The blood pressure watch 10 can be calibrated without use of a sphygmomanometer or access to trained personnel as illustrated in FIG. 1. Conventional smart watches include a heart rate sensor 12 that operate as pulse oximeters. Typically, what is used is an optical sensor that defines the velocity of blood flow in the sensed artery over a time period. The sensed velocity is then mathematically manipulated to calculate a corresponding blood pressure. The difference in available devices principally relies on using different LED wavelengths and proprietary signal processing software. The sensor 12 illuminates the skin and measures any changes in light absorption. Calibration of such a smart watch sensor 12 is performed using a self-contained module with a USB connection 14 that mates with the smartwatch 10. The module includes an LED oximeter simulator 16 driven with a known frequency and powered by a battery 18, a use indicator 20 that prevents the use of the simulator 16 more than predetermined number of times during a calibration interval, and a timing circuit that strobes the LED oximeter simulator 16 to simulate two known blood pressure readings which are input into the watch 10, namely a high and a low pressure. The decrement in voltage output of the battery 18 with each use is predetermined and the module is not used beyond its known initial battery plateau. For example, measurement may be intended for ten repetitions during a calibration interval during which battery voltage is reliably constant.

Figure 2:
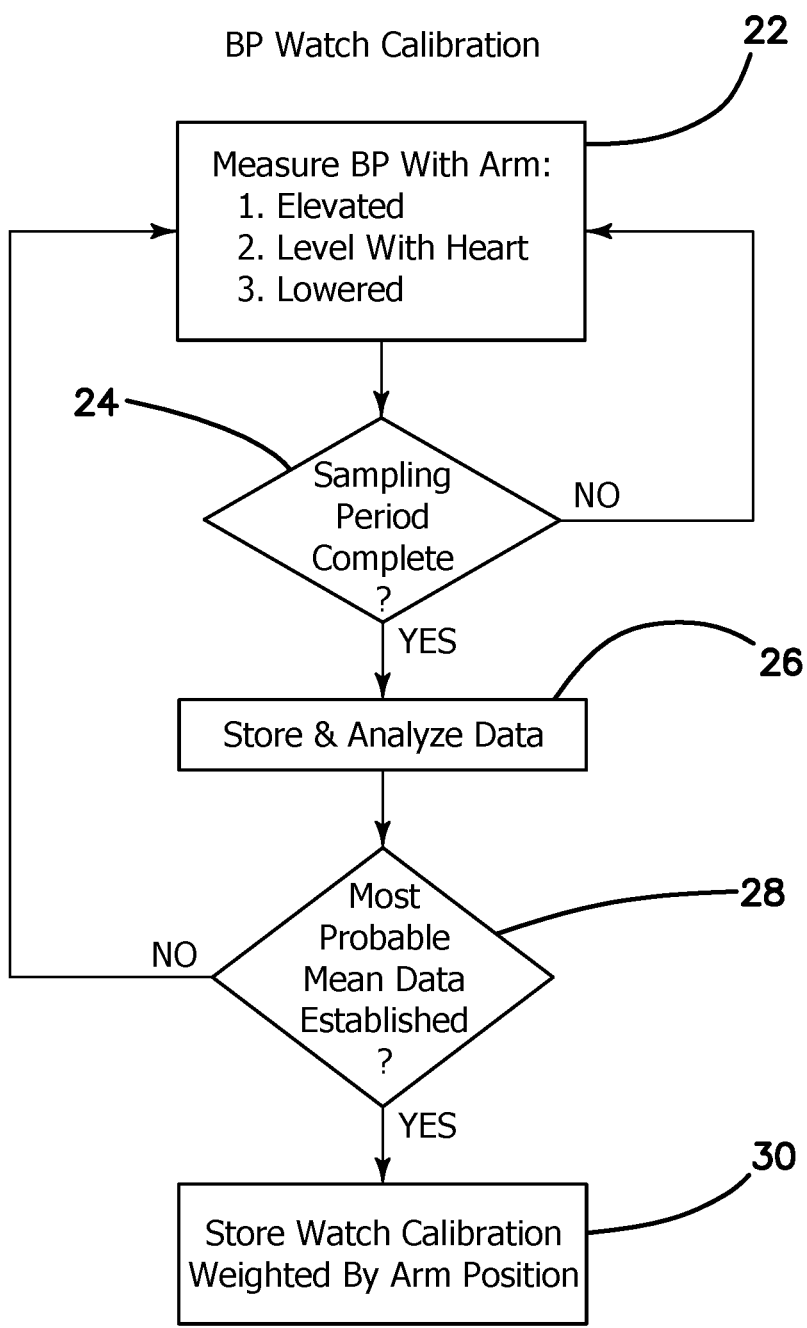
FIG. 2 is a flow diagram illustrating how the watch of FIG. 1 is calibrated for dynamic correction of the measured blood pressure depending on arm position over the course of time.

The smart watch 10 is also subject to secondary calibration based on a dynamic measurement of position of arm as measured by an accelerometer 13 as illustrated in the flow diagram of FIG. 2. The watch 10 on an arm held above the heart will have a lower measured blood pressure than when the arm is held below the heart, because of the differences in the distance from the pressure source, the heart, and the effect of gravity at step 22. The blood pressure is measured in a variety of positions, e.g. elevated, heart level and depressed height position of the arm and the measured value is stored in each arm position. The data sampling is repeatedly performed during a predetermined number of days (e.g. three) before therapy begins to create a database for the monitored patient as determined at step 24. The data is stored and analyzed to establish a mean, standard deviation (SD), other statistical measures of variability of blood pressure as a function of arm position as measured by an accelerometer included in the watch 10 at step 26. After period of data sampling, e.g. 3 days, a baseline primary measurement variability of the blood pressure measurements of the watch in response to three different body positions, such as arm above head, level with heart, and hanging at side. The separate datasets taken over the sampling period are compared in step 26 to determine what makes them significantly different from each other and therefore reliably distinguishable. Measurements are made during the sampling period, e.g. three full days, to determine real-life primary measurements which are characterized by the percentage (contribution) of each measurement to a master mean value that is a composite of all three basic arm positions.

The secondary calibration of the watch is repeated for the monitored patient until a common or most probable formula for the mean data is known and stored in step 28. This process is repeated several times a day, because daily-activity will be different than nighttime-sleeping with respect to arm position as compared to daytime until a 24 hour profile of blood pressure trend is known for the monitored patient at step 30. A trend is defined as the relative contribution of the secondary measurements as it affects the primary measurement of blood pressure by the watch for different times of the day. This calibration protocol contributes to measurement accuracy with the watch, which is otherwise regarded as notoriously inaccurate.

A quantitative example will assist in understanding how calibration of the secondary measurement of blood pressure works. Suppose the following data were established for a monitored patient.

| Morning | |
|---|---|
| Mean BP | 110 |
| Arm above | 3% |
| Arm neutral | 40% |
| Arm below | 57% |

Adjustment Weighted for Contribution of Arm Position 104

Positioning of the arm below the thorax will elevate blood pressure. The magnitude of the deviation depends upon the percentage time the arm is below the thorax. Similarly, arm above the thorax will lower blood pressure.

The protocol establishes at step 30 the most probable mean value for the primary measurement for three times of the day: morning, late afternoon, and while sleeping, and as a mean for entire 24 hour period. This will serve as the baseline for treatment (BAT). The blood pressure variability is calculated for the entire 24 hour period. Alternatively, PP will allow the physician to input three different BATs that can be applied for three different 8 hour periods. The protocol then establishes the desired change from the BAT, the goal of therapy for each treatment interval. The default value is the 24*h* mean. This can be by physician input, or a stored nomogram. The physician then Inputs the ideal time interval for the blood pressure change to take place. An acceptable rate of change (in the case of blood pressure, millimeters of mercury change per hour) during the treatment interval is then established by the treating physician.

PP Treatment Protocols

Figure 3:
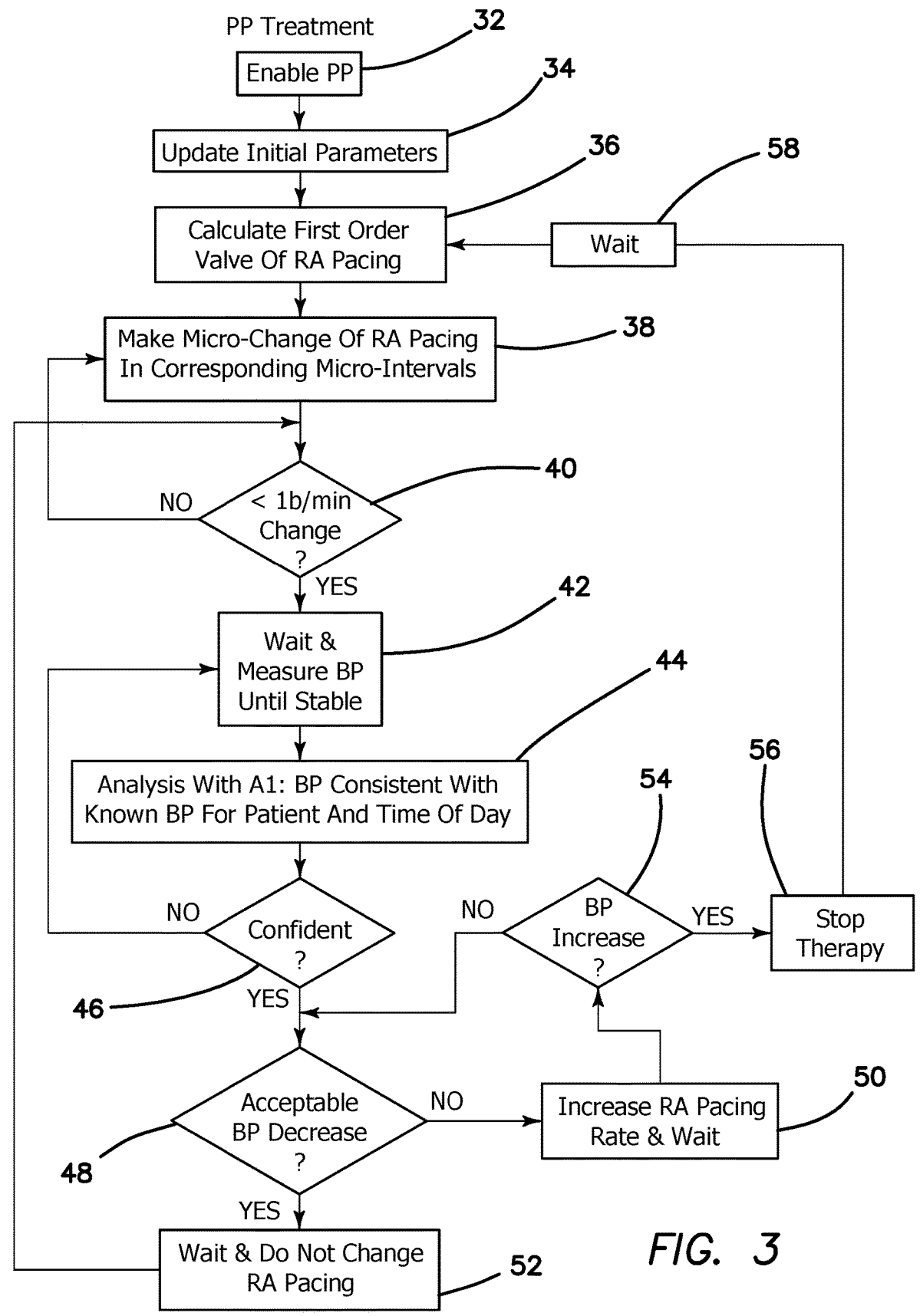
FIG. 3 is a flow diagram illustrating the actions and decisions made during a PressurePace (PP) treatment using artificial intelligence (AI).

A measurement is taken and therapy under the PressurePace algorithm (PP) is undertaken as set out in the flow diagram of FIG. 3. For example, treatment is adjusted according to a 24 hour mean blood pressure. The treatment algorithm (PressurePace) is enabled at step 32. The system updates PP with the BAT, the desired change, the interval of change, and the rate of change at step 34. PP calculates the first order value for RA pacing at step 36 to reach the treatment goal, regardless of the time of change, or the rate of change. This value is divided into a predetermined number of individual segments in a stair-step manner (e.g. 100), which are called the micro-intervals. PP instructs the pacemaker to begin with a ⅟₁₀₀ change in RA Pacing, the first micro-interval at step 38. If the first interval treatment calculates a less than 1-beat-per-minute change at step 40, which is the default change, wait a predetermined number of seconds (e.g. 3 sec) and measure blood pressure until a stable validated blood pressure is achieved at step 42. Using the blood pressure value after one treatment interval, perform a decision analysis using AI (or a machine-learning subroutine at step 44. Is the blood pressure measurement consistent with known blood pressure data from that patient at that time of day? If yes and confident as determined at step 46, proceed. If not, take another measurement at step 42 and repeat until there is "confidence" that the measurement is accurate. "Confidence" may be established by any predetermined measure, such as measurement within a predetermined or selected range. If treatment occurred, and the blood pressure went down by an amount within the acceptable rate of change and absolute value as determined at step 48, wait a predetermined number of minutes (e.g. 5 min), do not change the pacing rate as per step 52, and return to step 40. If the blood pressure didn't have an acceptable decrease at step 48, increase RA pacing by the second increment at step 50 (in this embodiment, up 2% of the maximal allowable change predicted by PP.) Wait 5 minutes and return to step 40 If the blood pressure went up instead of down (or the patient reported an adverse event by pushing a button on the blood pressure watch) at step 54, stop therapy at step 56 which means return to the RA Pacing rate that was present prior to beginning treatment. Suspend treatment and return to RA Pacing rate prior to treatment at step 36. Wait 5 minutes at step 58. Divide steps of treatment into 200 incremental steps (one half the prior values) at step 38 and repeat the treatment steps thereafter. If same negative result is obtained at step 48, suspend all treatment and alert and consult with the physician. If a positive result is obtained, or no change, proceed as before with the 50% value for the micro-interval treatments (e.g. 200 micro-intervals, which may increase the RA pacing rate).

The Protocol of PP Interaction with Rate Modulation (RM)

Figure 4:
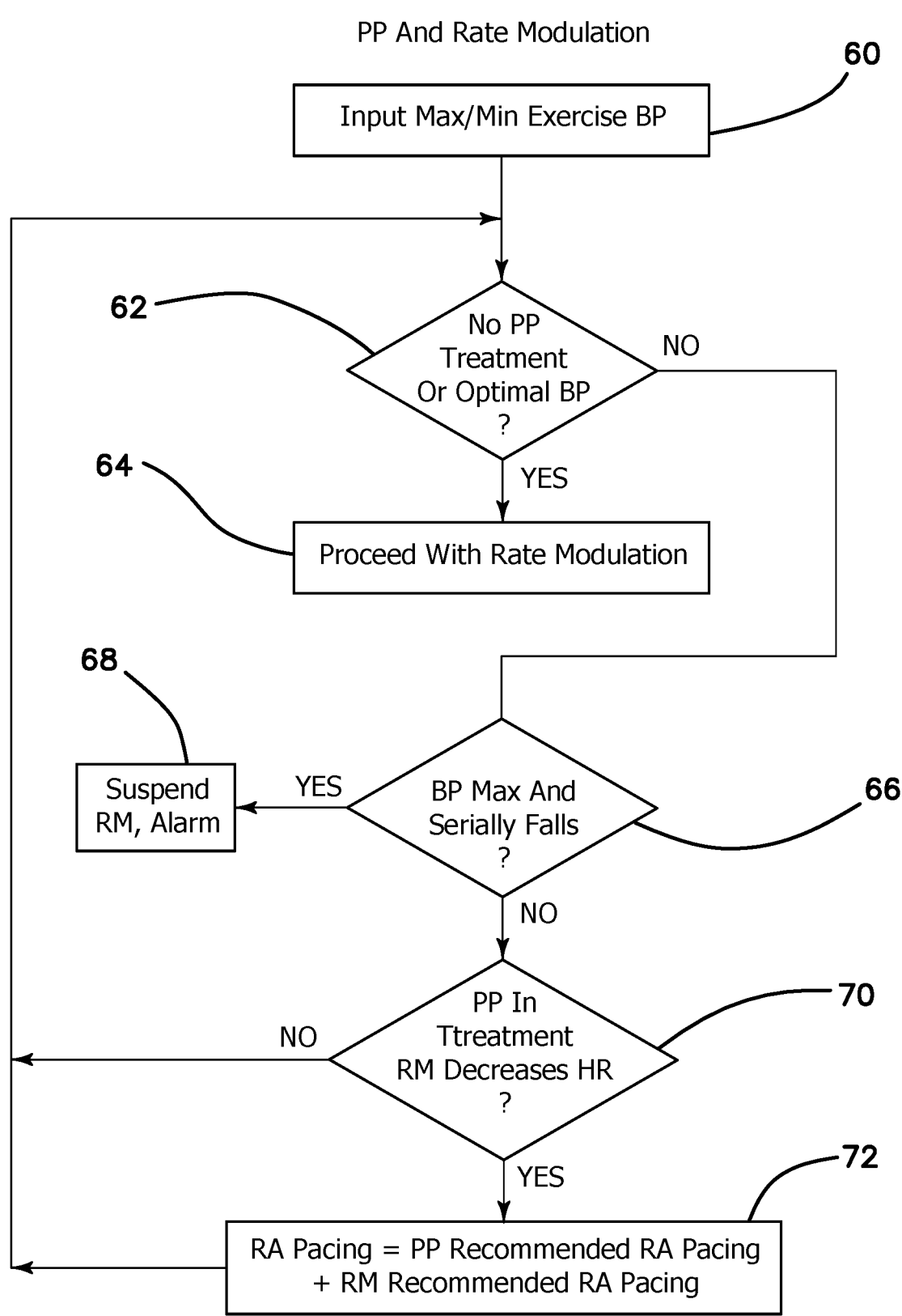
FIG. 4 is a flow diagram illustrating the actions and decisions made during a PressurePace (PP) treatment using artificial intelligence (AI) with rate modulation.

Rate-modulated pacemakers use a physiologic sensor other than the sinus node to adjust the pacing rate according to the physiologic needs of the patient. Increased RA pacing (RAP) caused by a change in rate modulation will occur during exercise in some patients, if this function is active and programmed by the attending physician as illustrated in the flow diagram of FIG. 4. This RM-induced increase in RA pacing may also lower blood pressure as is formally shown in treadmill protocols. The "ideal blood pressure", which is a 24 hr. blood pressure value upon which treatment is based, is different from the ideal blood pressure that occurs with exercise, which will be somewhat higher. The supervising physician determines the maximal and minimal accepted exercise blood pressure magnitudes at step 60. Blood pressure is considered a top hierarchy over exercise heart rate. PP will "observe" the blood pressure and commands recommended by rate modulation. If no PP treatment is in progress. e.g. blood pressure is considered optimal as determined at step 62, rate modulation is allowed to proceed as intended or programmed at step 64.

There are possible data permutations that require different actions. If blood pressure reaches the accepted maximum due to exercise and If blood pressure begins to fall on serial measurements as determined at step 66, possibly subject to a predefined absolute limit and rate of fall, rate modulation is suspended at step 68 with a predetermined slow down rate and duration of slow down and the patient is alarmed via the watch. If PP is in a treatment cycle, e.g. commands an incremental increase in heart rate being sent to pacer and blood pressure being monitored per PP algorithm, and if at the same time rate modulation directs a further increase in heart rate due to exercise and respiratory sensors at step 70, the following operation will be performed. The net RA pacing recommended by PP to achieve optimal blood pressure is set at the sum of the RA pacing recommended by PP and the RA pacing recommended by rate modulation at step 72. The process continues with step 62, TEB and OPTIVOL with PressurePace and AI Patients with pacemakers having OptiVol can be monitored by PressurePace and AI or at least a local machine learning subroutine, if patients with severe lung disease are excluded to keep RA pressure constant. OptiVol or TEB thus becomes useful for a new goal, namely as an indirect measure of SVR.

Nevertheless, there is a signal from OptiVol or TEB that tracks cardiac output when the patient is not in heart failure and does change in a predicted direction when heart failure develops. We use trending, not absolute values of measured output. SVR are better than skin electrode trends as SVR encompasses all the causative factors, not just ANS input to vascular resistance. Precise or accurate measurements of SVR are not required, but only trends of SVR, which OptiVol can supply for patients not in heart failure. The use of a trending AI-based algorithm where the direction of change in SVR for each increment of time is what is needed, more than an absolute value.

If we use a trending AI-based algorithm to calculate a trend in SVR, and the algorithm detects an increased bio-impedance over a matter of hours or days, the algorithm can signal the possible development of increased lung water. The patterns of changes in SVR due to pacing and blood pressure dynamics are very different than the slow onset of heart failure, absent a cardiac catastrophic event like a massive heart attack. PressurePace algorithm is "taught" the difference using AI between patterns of changes in SVR due to pacing and blood pressure dynamics and the slow onset of heart failure. The algorithm is always be on the lookout for this difference from moment to moment. Thus, OptiVol or TEB is used with PressurePace and AI to trend SVR to detect the occurrence of increased lung water or most likely heart failure. In one embodiment, a periodic data dump via a secure transfer to a remote server having AI is contemplated where updated analysis is done, and the existing treatment algorithms are refined. PP runs using machine learning for routine data accumulation and rules-based decision analysis, and periodically communicates to the cloud with an AI engine.

The ability to reliably measure SVR trends breaks down somewhat if RA pressure increases. An initial high, stable RA pressure has no adverse effect, rather only when the RA pressure changes. Even so, the magnitude of RA pressure is so small that it would likely make little difference. Increased lung water would also perturb the measurement by changing the trending to look like artificially increased SVR. But AI could detect such a trend by noting the rate of rise of the change which would be outside of what would be expected for SVR in the same patient. The AI would have an archive of typical SVR changes (moment to moment) of the monitored patient, and could easily detect an overlay trend that "moves" with a different pattern. The PressurePace algorithm with AI would already have been "taught" the kinds of patterns to expect with increased lung water.

To verify the disclosed methodology we would do a pilot study in parallel with what we call our chairside protocol with a first group of patients. Conventional bioimpedance TEB units are available to measure SVR or at least trends that are accepted as valid. A comparison with a second group of patients with Medtronic pacers and hypertension, whose pacemakers have OptiVol, are also monitored and run side by side with the first group as we increase RA pacing to change blood pressure. RA pacing would at least temporarily increase cardiac output for a few minutes until homeostasis sets in, and that would cause a drop in SVR. If OptiVol trends in the right direction along with the conventional TEB unit, a PressurePace algorithm with AI is then included to the pacing protocol: The combination of a blood pressure device, PressurePace with AI and OptiVol detects SVR changes as an adjunct to the real time closed-loop AI powered pacing system.

It is within the scope of the invention to use OptiVol to detect early increases in lung water by processing the OptiVol data in a different manner than previously used to predict heart failure.

Furthermore, since TEB and SVR can be integrated into a measure of cardiac output (even if not in the actual liters/min metric), a physiologic pacemaker as disclosed can be integrated into Implantable electronic cardiovascular devices (IECD's) for diagnostic or therapeutic treatment of heart failure, including but not limited to implantable cardioverter defibrillators (ICDs), cardiac resynchronization therapy devices with defibrillation capability (CRT-Ds) and cardiac resynchronization therapy pacemaker (CRT-P's). The use of trending measurements of SVR allows the real time use of conventional blood pressure wrist watches, which are inaccurate and inexpensive, for much smoother changes in pacing rate and hence in a physiologic response. Use of Systemic Vascular Resistance (SVR) Derived from an OptiVol Pacemaker (Medtronic, Minneapolis, MN).

Figure 5:
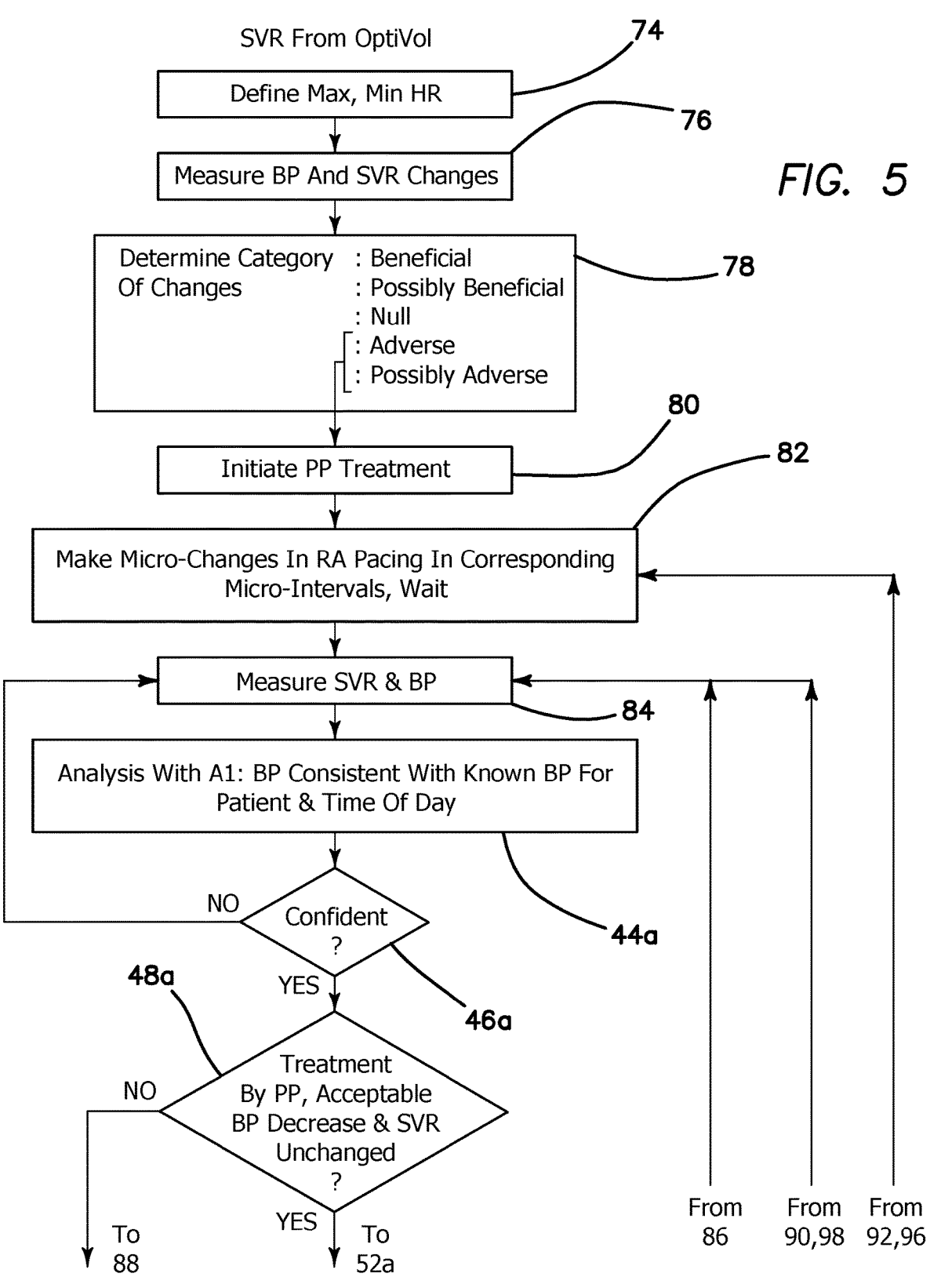
FIG. 5 is a flow diagram illustrating the actions and decisions made during a PressurePace (PP) treatment using artificial intelligence (AI) with an OptiVol equipped pacemaker or a pacemaker with similar or equivalent thoracic electrical bioimpedance (TEB) measuring capability.
Figure 5:
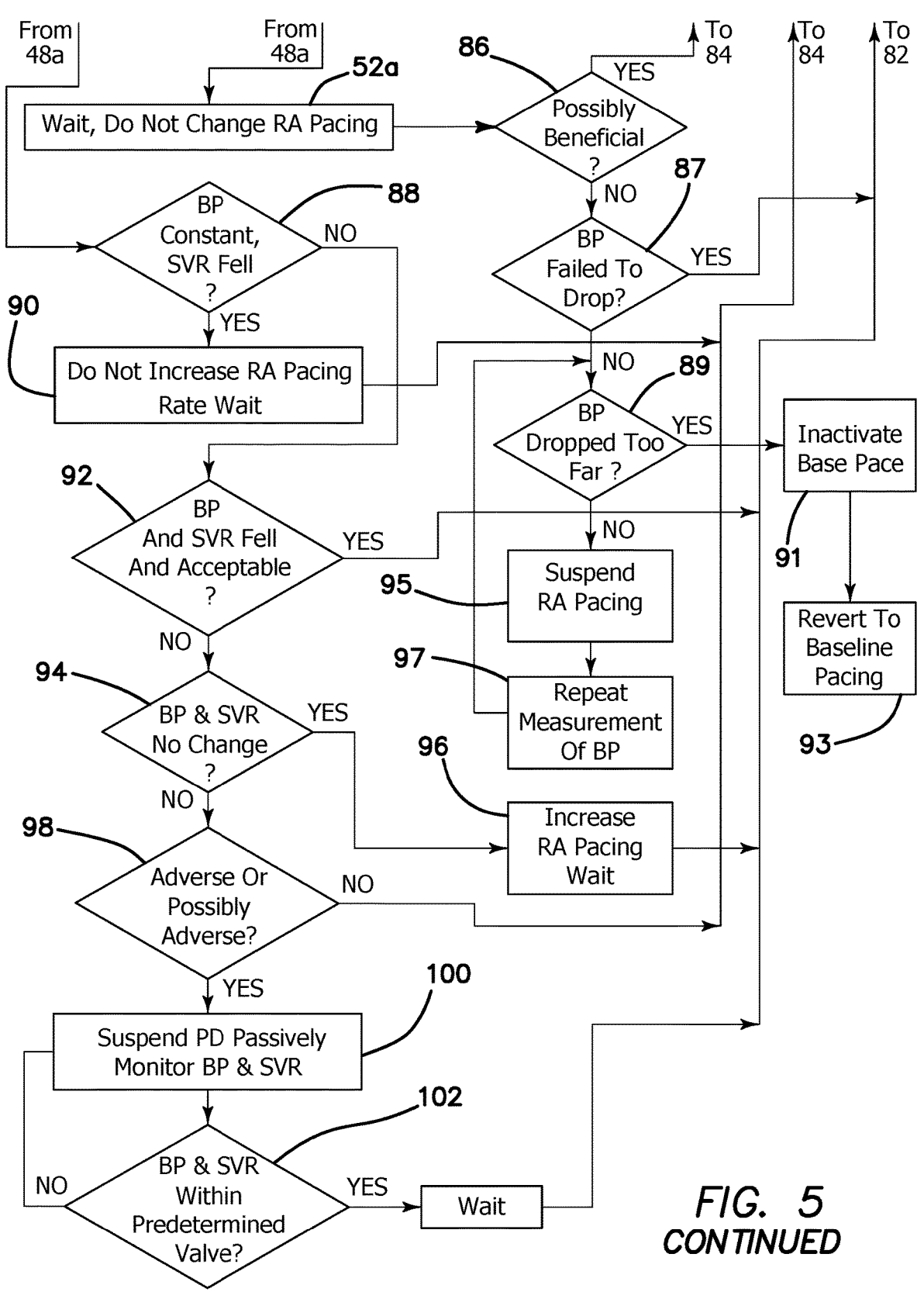

In the flow diagram of FIG. 5 we assume that: right atrial pressure is presumed to be constant at 10 mmHg; baseline OptiVol sensor output has been collected and analyzed over a predetermined number of days, e.g. three days, in the same manner as blood pressure; blood pressure remains at the top of the hierarchy; heart rate is second in hierarchy, and takes over only if PP determines to suspend RA pacing because of falling blood pressure; and the SAA algorithm (see incorporated specifications) is not active. The sensor inputs include blood pressure from watch 10, SVR using OptiVol in the conventional calculation based on the cardiac output variable, heart rate from the pacemaker, respiratory rate from the pacemaker (not shown), and an accelerometer (not shown) in the pacemaker.

The protocol then defines the maximum and minimum heart rates at step 74. The minimum is selected by the supervising physician and cannot be <40 for all types of pacemakers. The maximum is an intrinsic or not pacemaker assisted heart rate at which point the pacemaker no longer stimulates. The questions then arise: What is the optimal blood pressure at rest; What is the upper limit of blood pressure; What is the lower limit of blood pressure; What is the optimal percentage increase in blood pressure with exercise; What is the BAT (if it has been determined); What is the baseline "SVR" value using the BAT to calculate mean arterial pressure. The units of SVR are meaningless.

The goal is to optimize both blood pressure and SVR over a 24 hour period. A drop in SVR is considered crucial to prevent and treat all forms of heart failure. Blood pressure varies with a diurnal pattern, high in the morning, and lower at night. Moreover, the use of medications complicates this further, and depends on the individual medications absorption, dosing, release kinetics, as well as other drug parameters. A key advantage of the illustrated embodiments are that they are dynamic and make treatment decisions throughout the day, at rest and with activity. This dynamic quality also allows us to study the effect of interventions, such as medications, to better understand their treatment profiles for each patient over a variety of circumstances, including time of day and rest versus activity.

There are a number of possible permutations of the data that will govern "treatment" decisions arising from a measurement at step 76. For every blood pressure change (down, no change, up), there are three possible accompanying SVR values (down, no change, up) for a total of nine combinations. These datasets can be classified at step 78 as beneficial, null, or adverse respectively. We can further categorize as possibly beneficial or possibly adverse, both resulting in a wait and watch cycle to look for further trends.

Consider some examples of categories.

| Category of Data Changes | Characteristics |
| --- | --- |
| Beneficial: | The optimal response would be a fall in blood pressure to the desired level accompanied by a fall in SVR. |
| Possibly Beneficial: | Another example of positive response would be no change in blood pressure and a drop in SVR. |
| Null: | No change in blood pressure or SVR is a null data set. |
| Adverse: | A drop in blood pressure outside of acceptable limits accompanied by a rise in SVR units, or an increase in blood pressure accompanied by an increase in SVR units |
| Possibly Adverse | A drop in blood pressure outside of acceptable limits with no change in SVR or an increase in blood pressure without change in SVR units. |

Once the category is determined, treatment is initiated at step 80 if the category is adverse or possibly adverse. When treatment is initiated the PP treatment algorithm (PressurePace) is enabled. PP is updated with the BAT, the desired change, the interval of change, and the rate of change. PP determines the first order value for RA pacing to reach the goal. This value is divided into a predetermined number of individual segments in a stair-step manner, e.g. 100 segments, called the micro-intervals. PP instructs the pacemaker to begin with a 1/100 change in RA pacing in the first micro-interval at step 82. Wait a predetermined number of seconds (e.g. 3) and measure blood pressure and SVR units at step 84.

Then analysis and branch logic follows using AI in a manner similar to that disclosed in FIG. 3 with respect to steps 44-58. Is the blood pressure measurement used for treatment decisions consistent with known blood pressure data from that patient at that time of day as determined at step 44*a*? If yes and confident at step 46*a*, proceed. If not, take another measurement at step 84 and repeat until there is "confidence" that the measurement is accurate similar to described above or as determined by machine learning. If treatment occurred, and the blood pressure went down by an amount within the acceptable rate of change and absolute value, but SVR units were unchanged at step 48*a*, wait a predetermined number of minutes (e.g. 5 min), do not change the pacing rate at step 52*a*, and return to step 84 if possibly beneficial as determined at step 86.

If the result of the increase in RA pacing is not beneficial at step 86, this could have two meanings: 1) The BP failed to go down the amount pre-defined as a successful outcome as determined at step 87, which would require an additional treatment by returning to step 82; or 2) the BP went down too far as determined at step 89, which would be a pre-defined value below which the BP would not be allowed to fall. This would result in a suspension of RA pacing at step 95 and a repeat BP measurement at step 97. If the BP was still too low as determined at step 89, the PressurePace algorithm would inactivate as step 91 and the pacemaker would default to baseline programming at step 93. If the blood pressure didn't change, but SVR fell as determined at step 88, do not increase pacing rate and re-evaluate in 5 minutes at step 90. This assumes that a drop in SVR is beneficial, and blood pressure may lag behind, another possibly beneficial response. If blood pressure and SVR fell and are within acceptable limits as determined at step 92, this is definitely beneficial and move to the next micro interval at step 82 provided that the tests for rate of change and absolute value of blood pressure have been met. If blood pressure didn't change, and neither did SVR as determined at step 94, increase RA pacing by the second increment, e.g. up 2% of the maximal allowable change predicted by PP at step 96. Wait 5 minutes and return to step 82.

If any of the events classified as adverse or possibly adverse occur, or the patient signals that he/she isn't feeling well at step 98, suspend PP at step 100. Any intervention that causes the patient to signal that he/she doesn't feel well automatically suspends PP until reactivated by physician. Blood pressure and SVR will continue to be monitored passively. If predefined emergent levels of either are noted, the system audibly alarms for three seconds and a text message is sent to a control center or to the doctor's phone if so authorized. Assuming no patient activated alarm, the program remains active. It will wait 5 minutes and consider resuming treatment with step 82. Treatment will not resume unless blood pressure and SVR return to within a predetermined percentage (e.g. 70%) of pre-treatment values as determined at step 102. Monitoring is continued until blood pressure and SVR return to within the predetermined percentage is achieved. If this has occurred:

In the case of a return to step 82 divide steps of initial programmed treatment into 200 incremental steps (which results in one half of the prior values) and repeat treatment algorithm following step 82. If same negative result is obtained at step 102 a second time, suspend all treatment and consult with physician. If a positive result, a potentially positive result, or no change, proceed as with step 82 with the 50% value for the micro-interval treatments (increases in RA pacing rate).

Steady-State Treatment

At some point, the goal blood pressure and a lowered SVR should be achieved. When this occurs, the system will be in monitor-only mode. When the desired endpoint is reached (ideal blood pressure), no further treatment intervals are commenced and RA pacing remains unchanged. If the blood pressure continues to fall, the process is reversed and the RA pacing rate is reduced by the same increments and timing until it stabilizes at the desired value. If blood pressure continues to fall and RA pacing rate is reduced to the point that the heart rate is now at the lowest permissible value (the pacemaker's lower rate limit set by physician) an audible alarm occurs and messages are sent.

PressurePace and Blood Pressure Watch Protocols

Figure 6:
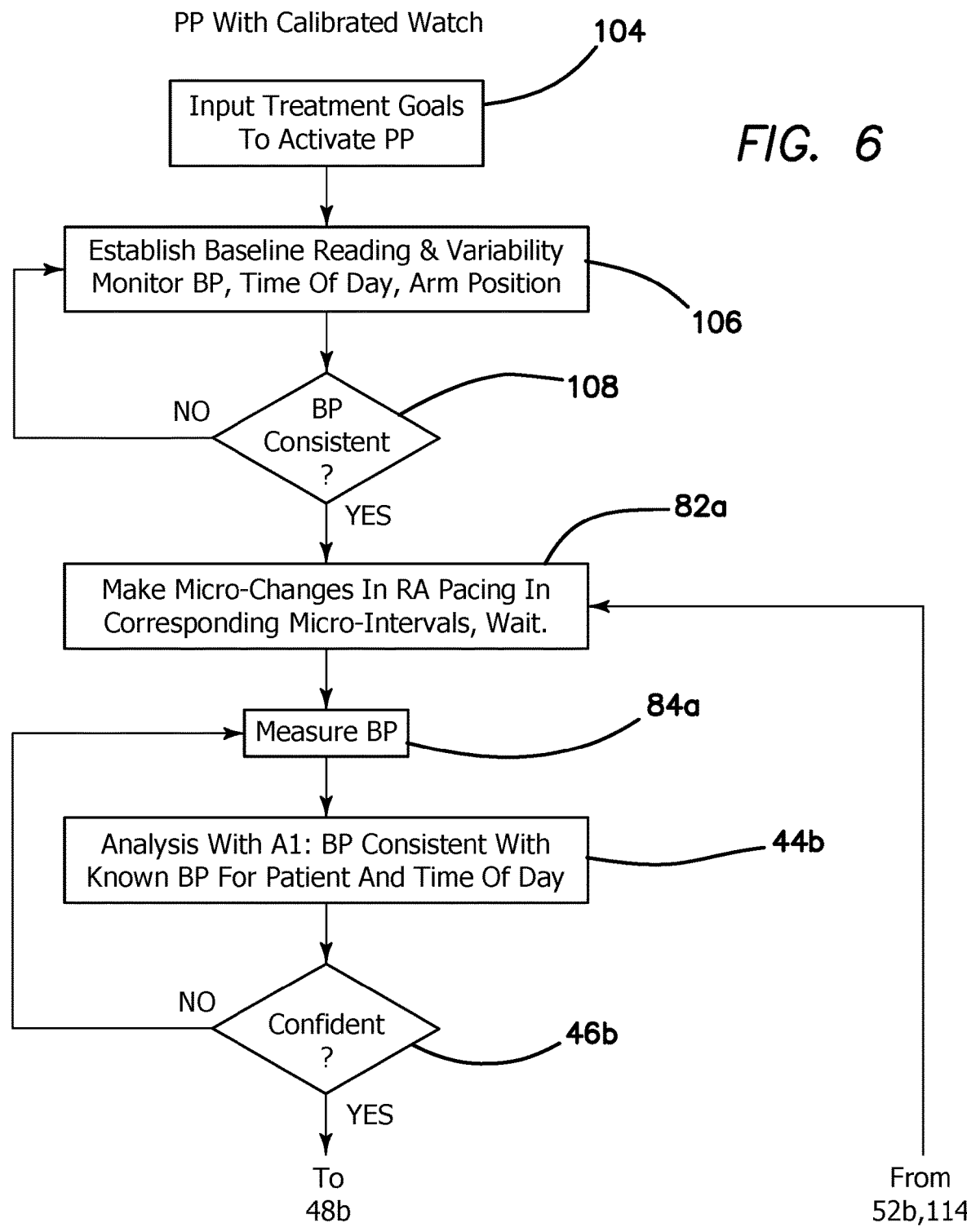
FIG. 6 is a flow diagram illustrating the actions and decisions made during a PressurePace (PP) treatment using artificial intelligence (AI) with an electronically calibrated watch or a watch corrected for dynamic arm position.
Figure 6:
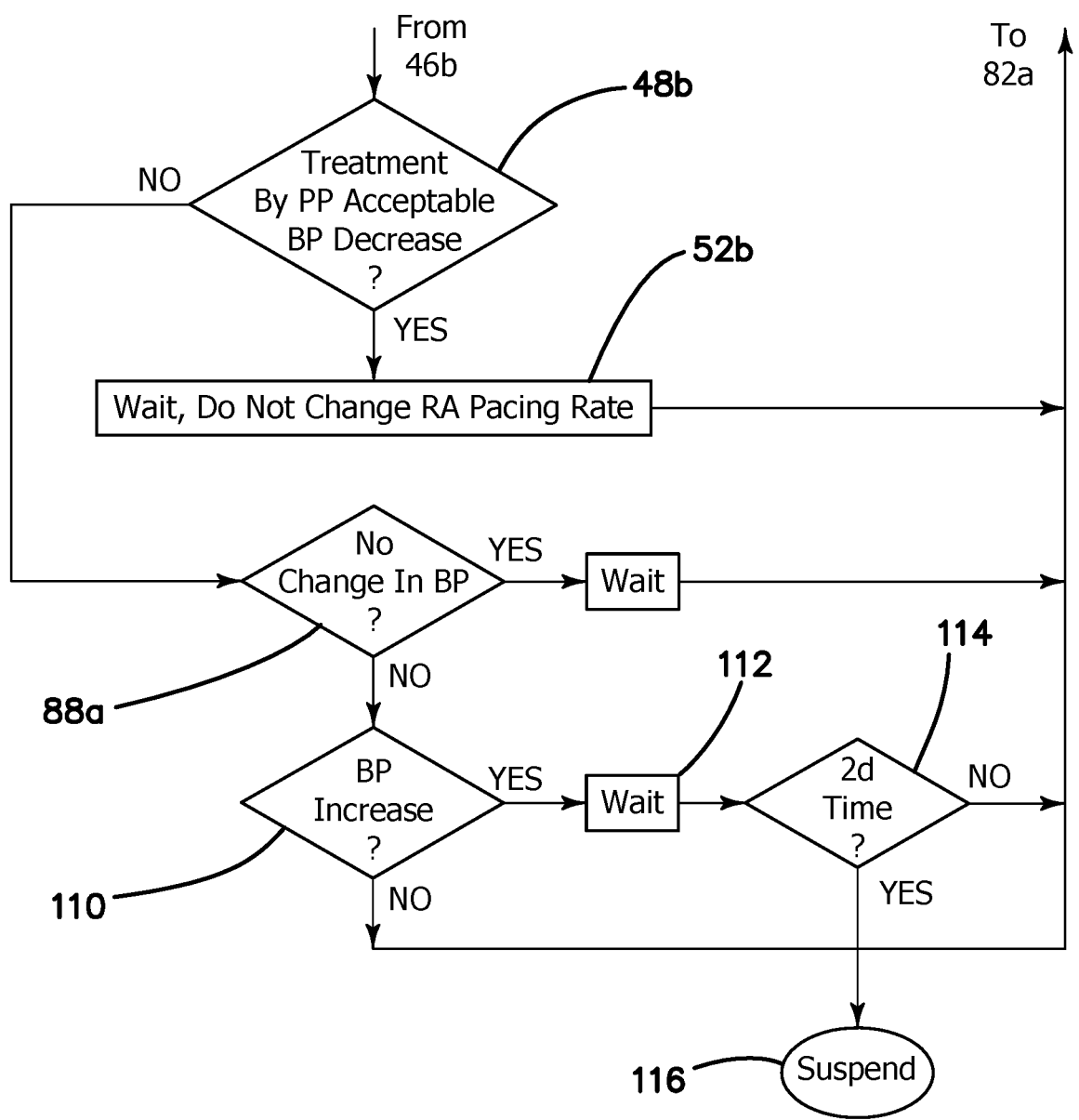

Consider now the decision flow for the treatment of blood pressure using PressurePace PP and the secondarily calibrated blood pressure watch 10 as illustrated in the flow diagram of FIG. 6. At step 104 the supervising physician inputs treatment goals to PressurePace where the rate modulation parameters are preset. The protocol continues with the following steps. Establish baseline readings and determine measurement variability. Initiate treatment by activating PressurePace PP. Monitor blood pressure, correct for time of day and arm position based on prior data at step 106. Validate baseline readings. If blood corrected pressure measurement is consistent with known data at step 108, proceed to treatment. If corrected blood pressure measurement is not consistent, repeat the steps of monitoring/validating at step 106.

When treatment is initiated PP determines the first order value for RA pacing to reach the goal, regardless of the time of change, or the rate of change. Similar to FIG. 5 at step 82*a* in FIG. 6 this value is divided into a predetermined number of individual segments, e.g. 100, in a stair-step manner, called the micro-intervals. PP instructs the pacemaker to begin with a $1/100$ change in RA Pacing, the first micro-interval. Wait a predetermined number of seconds (e.g. 3) and measure corrected blood pressure at step 84*a*.

Then analysis questions and branch logic at step 44*b* follows with AI similar to steps 44-58 of FIG. 3. The following questions arise: Is the corrected blood pressure measurement consistent with known corrected blood pressure data at step 44*b* from that patient at that time of day. If confident at step 46*b*, proceed. If not, take another measurement at step 84*a* and repeat until there is "confidence" that the measurement is accurate. If treatment occurred, and the corrected blood pressure went down by an amount within the acceptable rate of change and absolute value as determined at step 48*b*, wait a predetermined number of minutes (e.g. 5), do not change the pacing rate at step 52*b*, and return to step 82*a*. If the corrected blood pressure didn't change as determined at step 88*a*, increase RA pacing by the second increment (e.g. up 2% of the maximal allowable change predicted by PP.) by returning to step 82*a* after a wait of 5 minutes.

If the corrected blood pressure went up instead of down or the patient reported an adverse event by pushing a button on the corrected blood pressure watch as determined at step 110, stop therapy which means returning to the RA pacing rate that was present prior to beginning treatment at step 82*a*. Wait 5 minutes at step 112. Divide steps of treatment into 200 incremental steps (one half the prior values) and return to step 82*a*. If same negative result is obtained as second time as determined at step 116, suspend all treatment and consult with physician. If a positive result or no change, return to step 82*a* as before with the 50% value for the micro-interval treatments (increases in RA pacing rate). If treatment goal has been achieved without negative outcomes, begin steady-state treatment algorithm. In either Treatment or Steady-State modes, rate modulation is always subordinated to PP according to the above protocols.

Microtrending

In contrast with conventional proactive therapies which data mine electronic health data, such as shown in U.S. Pat. No. 9,208,284, the disclosed embodiments may be used: to perform micro-trend analysis; to function at the point of care in real-time, as opposed to retrospective data-mining; to form an autonomous prospective treatment loop; to perform active treatment and not merely make predictions and a set of probabilities to be studied and used in population analysis or the formation of guidelines; to provide near instantaneous treatment decisions with real-time updates; and to allow patient contribution of subjective inputs to the data set in real-time The disclosed system could be characterized as a system which gathers three sets of data in real-time, namely physiologic data from a sensor platform, including BP and other measured inputs; physiologic parameters from a pacemaker, such as HR, accelerometer, respiratory rate, and OptiVol sensed data; and patient-derived data, i.e. the patient's subjective input These three data sets are inputted to a so-called "black box" machine learning module that has been fed these variables and has learned how to recognize the best dataset to achieve the optimum blood pressure result and an ideal set of other physiologic parameters, including the patient's best sense of wellbeing to calculate a master best-possible parameter set for treatment. The system initiates treatment in a micro-trend format, then observes the results for each small interval, makes adjustments, learns more, and treats again, or suspends treatment. The treatment process loops back and repeats. The treatment process operates autonomously. The disclosed treatment method differs from standard health data mining and predictions for health maintenance for the following reasons: a) the use of micro-trend analysis; b) functions in real-time; operates as an autonomous prospective treatment loop; provides active treatment, not predictions and a set of probabilities to be studied and used in population analysis or the formation of guidelines. The patient contributes subjective inputs to the data set in real-time as part of the treatment.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

The invention claimed is:

1. A computing device, comprising at least one processor and at least one memory comprising instructions that, when executed by the at least one processor, cause the computing device to perform operations comprising:

determining, from a velocity of blood flow sensed by an optical sensor of a wearable device, a first blood pressure value and a subsequent blood pressure value of a patient;

receiving, via a wireless interface, the first blood pressure value and the subsequent second blood pressure value from the wearable device comprising an optical sensor;

receiving a first systemic vascular resistance (SVR) value and a subsequent second SVR value;

determining a change in blood pressure based on the first blood pressure value and the second blood pressure value;

determining a change in SVR based on the first SVR value and the second SVR value;

determining a pacing rate based on the change in blood pressure and the change in SVR;

administering a first initial micro-interval pacing rate to the patient via a pacing device based on the pacing rate;

receiving a third blood pressure value and a third SVR value in response to providing the first initial micro-interval pacing rate;

providing the third blood pressure value and third SVR to an artificial intelligence module trained to output a patient blood pressure category, wherein the artificial intelligence module is trained based on historical patient blood pressure data;

receiving an artificial intelligence module output from the artificial intelligence module, the artificial intelligence module output comprising a patient blood pressure category;

determining a pacing action based on the patient blood pressure category; and administering the pacing action to the patient via the pacing device.

2. The computing device of claim 1, wherein determining the pacing rate is in response to identifying an adverse event based on the change in blood pressure and the change in SVR.

3. The computing device of claim 2, wherein identifying the adverse event comprises one of:

identifying a drop in blood pressure based on the change in blood pressure and identifying a rise in SVR based on the change in SVR;

identifying an increase in blood pressure based on the change in blood pressure and identifying the rise in SVR;

identifying a drop in blood pressure below a minimum blood pressure and identifying a stable SVR based on the change in SVR; or identifying the increase in blood pressure and identifying the stable SVR.

4. The computing device of claim 1, wherein a micro-interval of the first initial micro-interval pacing rate is a fraction of the pacing rate.

5. The computing device of claim 1, wherein the patient blood pressure category is selected from one of a decrease in blood pressure by a successful amount, a decrease in blood pressure by an unacceptable amount, or a stable blood pressure.

6. The computing device of claim 5, wherein the determining the pacing action based on the patient blood pressure category being the decrease in blood pressure by a successful amount comprises:

receiving a third SVR; and determining the pacing action is one of suspending the operations based on the third SVR meeting a target SVR, providing a second initial micro-interval pacing rate based on the third SVR not meeting the target SVR.

7. The computing device of claim 5, wherein the pacing action based on the patient blood pressure category being the decrease in blood pressure by an unacceptable amount comprises suspending the operations.

8. The computing device of claim 5, wherein determining the pacing action based on the patient blood pressure category being the stable blood pressure comprises:

receiving a third SVR; and determining the pacing action is providing an updated micro-interval pacing rate based on the third SVR indicating a stable SVR.

9. The computing device of claim 8, wherein the updated micro-interval pacing rate is greater than the first initial micro-interval pacing rate.

10. A method for cardiac pacing, the method comprising:

determining, from a velocity of blood flow sensed by an optical sensor of a wearable device, a first blood pressure value and a subsequent blood pressure value;

receiving, via a wireless interface, the first blood pressure value and the subsequent second blood pressure value from the wearable device;

receiving a first systemic vascular resistance (SVR) value and a subsequent second SVR value;

determining a change in blood pressure based on the first blood pressure value and the second blood pressure value;

determining a change in SVR based on the first SVR value and the second SVR value;

determining a pacing rate based on the change in blood pressure and the change in SVR;

administering a first initial micro-interval pacing rate based on the pacing rate;

receiving a third blood pressure value and a third SVR value in response to providing the first initial micro-interval pacing rate;

providing the third blood pressure value and third SVR to an artificial intelligence module trained to output a patient blood pressure category, wherein the artificial intelligence module is trained based on historical patient blood pressure data;

receiving an artificial intelligence module output from the artificial intelligence module, the artificial intelligence module output comprising a patient blood pressure category;

determining a pacing action based on the patient blood pressure category; and administering the pacing action to the patient via the pacing device.

11. The method of claim 10, wherein the patient blood pressure category is selected from one of a decrease in blood pressure by a successful amount, a decrease in blood pressure by an unacceptable amount, or a stable blood pressure.

12. The method of claim 11, wherein the determining the pacing action based on the patient blood pressure category being the decrease in blood pressure by a successful amount comprises:

receiving a third SVR; and determining the pacing action is one of suspending the cardiac pacing based on the third SVR meeting a target SVR, providing a second initial micro-interval pacing rate based on the third SVR not meeting the target SVR.

13. The method of claim 11, wherein the pacing action based on the patient blood pressure category being the decrease in blood pressure by an unacceptable amount comprises deactivating the cardiac pacing.

14. The method of claim 11, wherein determining the pacing action based on the patient blood pressure category being the stable blood pressure comprises:

receiving a third SVR; and determining the pacing action is providing an updated micro-interval pacing rate based on the third SVR indicating a stable SVR.

\* \* \* \* \*